(12) United States Patent
Voute

(10) Patent No.: US 9,139,348 B2
(45) Date of Patent: Sep. 22, 2015

(54) POUCH WITH INCORPORATED LOSS OF INTEGRITY INDICATOR, METHOD FOR MAKING SUCH A BAG, AND METHOD FOR USING SAME

(75) Inventor: Nicolas Voute, Cuges les Pins (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 276 days.

(21) Appl. No.: 13/378,369

(22) PCT Filed: Jun. 14, 2010

(86) PCT No.: PCT/FR2010/051182
§ 371 (c)(1),
(2), (4) Date: Jan. 26, 2012

(87) PCT Pub. No.: WO2010/146296
PCT Pub. Date: Dec. 23, 2010

(65) Prior Publication Data
US 2012/0128275 A1    May 24, 2012

(30) Foreign Application Priority Data

Jun. 18, 2009    (FR) ..................................... 09 54096

(51) Int. Cl.
B65D 33/00    (2006.01)
B65D 79/02    (2006.01)
(Continued)

(52) U.S. Cl.
CPC ................ B65D 79/02 (2013.01); B65D 77/04 (2013.01); B65D 81/2084 (2013.01)

(58) Field of Classification Search
CPC ... B65D 77/04; B65D 81/2084; G01N 21/783
USPC ........... 206/213.1, 205, 438, 439, 363; 383/5, 383/105, 120, 40
See application file for complete search history.

(56) References Cited

U.S. PATENT DOCUMENTS 4,098,577 A * 7/1978 Halpern ........................... 436/1
4,120,445 A * 10/1978 Carrier et al. ............... 206/459.1
(Continued)

FOREIGN PATENT DOCUMENTS

FR          2 252 619 A1    6/1975
WO          96/12659 A1     5/1996
(Continued)

OTHER PUBLICATIONS

International Search Report, dated Oct. 21, 2010, from corresponding PCT application.

*Primary Examiner* — Steven A. Reynolds
(74) *Attorney, Agent, or Firm* — Young & Thompson

(57) ABSTRACT

A pouch includes: a first closed, inner casing, made of at least one non-porous plastic material with a high-capacity gas barrier, delimiting a first space, forming a pouch stricto sensu for accommodating a biopharmaceutical product or device, a second closed, outer casing, made of at least one non-porous plastic material with a high-capacity gas barrier, delimiting a second space in which the pouch stricto sensu is located, spacer elements, at least one selected tracer gas, located in the first or second space outside of the pouch stricto sensu, with a higher partial pressure than in the second space outside of the pouch stricto sensu or in the first space, at least one colorimetric detector located, respectively, in the second space outside of the pouch stricto sensu or in the first space responsive to the concentration of the tracer gas, by switching from a first color to a second different color.

25 Claims, 2 Drawing Sheets

(51) Int. Cl.
*B65D 77/04* (2006.01)
*B65D 81/20* (2006.01)

(56) References Cited

U.S. PATENT DOCUMENTS

| | | | |
|---|---|---|---|
| 4,434,893 A * | 3/1984 | Barlow | 206/522 |
| 4,436,203 A | 3/1984 | Reyner | |
| 4,449,632 A * | 5/1984 | Marusiak, Jr. | 206/540 |
| 4,813,541 A * | 3/1989 | Velasco et al. | 206/459.1 |
| 4,986,429 A * | 1/1991 | Singleton, Jr. | 215/230 |
| 5,129,520 A * | 7/1992 | Gaspar | 206/534 |
| 5,988,422 A | 11/1999 | Vallot | |
| 6,119,855 A * | 9/2000 | Yeager et al. | 206/213.1 |
| 6,196,056 B1 | 3/2001 | Ewing et al. | |
| 6,793,076 B1 * | 9/2004 | Luo et al. | 206/521 |
| 6,840,372 B2 * | 1/2005 | Giles et al. | 206/216 |
| 6,892,567 B1 | 5/2005 | Morrow | |
| 7,207,154 B2 * | 4/2007 | Araujo | 53/410 |
| 2002/0147091 A1 * | 10/2002 | Healy et al. | 493/213 |
| 2004/0264813 A1 * | 12/2004 | Steffens | 383/5 |
| 2007/0110340 A1 * | 5/2007 | Buchman | 383/5 |
| 2007/0220956 A1 | 9/2007 | Terentiev | |

FOREIGN PATENT DOCUMENTS

| | | |
|---|---|---|
| WO | 00/04131 A1 | 1/2000 |
| WO | 01/04624 A1 | 1/2001 |

* cited by examiner

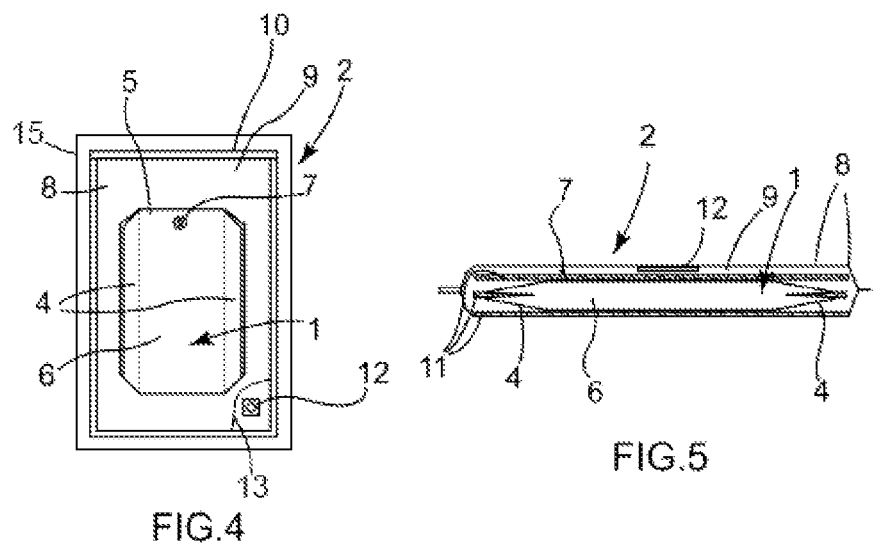
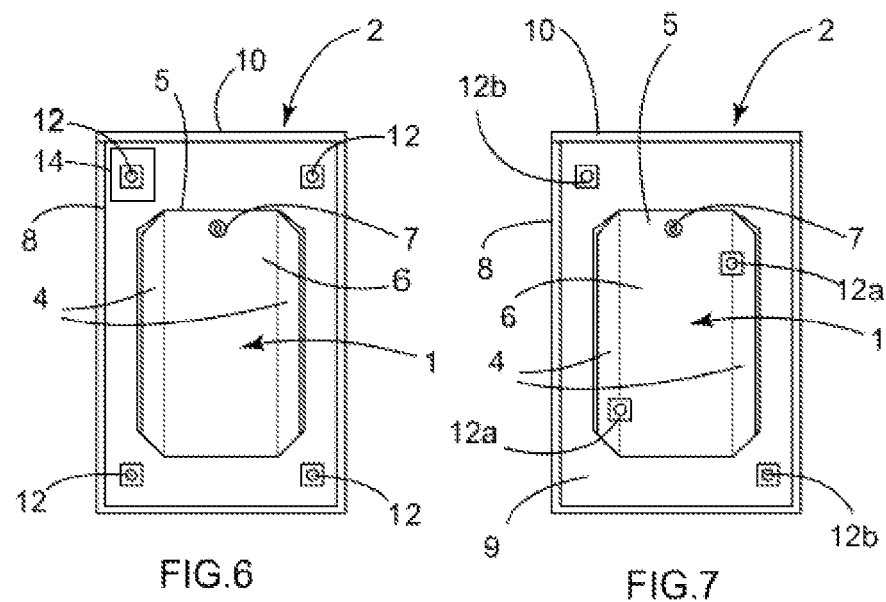

POUCH WITH INCORPORATED LOSS OF INTEGRITY INDICATOR, METHOD FOR MAKING SUCH A BAG, AND METHOD FOR USING SAME

BACKGROUND OF THE INVENTION

1. Field of the Invention

The invention relates to the detection of a possible loss of integrity of a closed, non-porous, flexible plastic pouch, such as a sterile pouch that is designed to accommodate a biopharmaceutical product or device or the like.

The purpose of the invention is more especially a pouch with an incorporated loss of integrity indicator that is active per se, and, after the pouch is manufactured and at least before the time when a biopharmaceutical product or device is to be introduced thereinto, the application of such a pouch with an incorporated and active loss of integrity indicator for creating a pouch stricto sensu that has all of its integrity and that contains the biopharmaceutical product or device, with such a pouch stricto sensu having its full guarantee of integrity, specially designed to contain a biopharmaceutical product or device, a process for the production of a pouch with an incorporated and active loss of integrity indicator, and, finally, a process relative to pouches stricto sensu that is specially designed to contain a biopharmaceutical product or device and having to exhibit a full guarantee of integrity.

2. Description of the Related Art

Here, a biopharmaceutical product is defined as a product that is obtained from biotechnology—culture media, cellular cultures, buffer solutions, artificial nutrition liquids, blood products, and derivatives of blood products—or a pharmaceutical product or more generally a product that is designed to be used in the medical field. Biopharmaceutical device is defined as a device that is designed to be implemented in a process of the biological or pharmaceutical field—measuring or checking means, means for treatment of a biopharmaceutical product, containers or parts of containers, means of transfer or closing. Such biopharmaceutical products or devices have high added value, and it is important that their integrity be ensured, in particular the absence of any contamination.

For the purposes of storage or shipping, it is common to place such biopharmaceutical products or devices in pouches that are closed and sterile, flexible, disposable, and made of non-porous plastic (such as polyethylene or a complex that comprises polyethylene) and that comprise at least one port or access that can be opened at the desired time.

Such pouches are known whose two large walls are directly joined to one another. Once expanded, such pouches have a limited volume and are relatively thin, which justifies the fact that they are often called "pillow" pouches or "2D" (D meaning dimensions) pouches. 3D pouches are also known that comprise two end walls and a side wall that can be folded flat and deployed unfolded, welded to one another, with the volume then being able to be at least 50 liters up to 3,000 liters, and even more. Such 3D pouches are described in the document WO00/04131 or marketed by the Sartorius Company under the trademark FLEXEL® 3D.

It is essential that such pouches, once manufactured and when they receive the biopharmaceutical products or devices mentioned above, be airtight, or at least have a degree of sealing that is deemed satisfactory. It is therefore essential to be able to detect any possible loss of integrity of such pouches.

Processes and devices for checking integrity of such pouches implemented online on all of the pouches during their manufacturing are known. Thus, the Standard F 2095-01 of ASTM International whose title is "Standard Test Methods for Pressure Decay Leak Test for Nonporous Flexible Packages with and without Restraining Plates" relates more specifically to the so-called pressure drop process. This process is considered according to two possible embodiments, namely with or without expansion-limiting plates.

In the embodiment with expansion-limiting plates, the procedure is as follows:

In a preparation phase:
  A pouch to be checked that has at least one port that can be sealed or connected in an airtight and removable way is provided,
  A pressurized gas source that is designed to be introduced into the pouch via the port is provided,
  Means for measuring the pressure of the gas in the pouch via the port are provided,
  Two fixed expansion-limiting plates that are separated and face one another and that will not conceal a possible leak in the large walls of the pouch placed against them are provided,
  The pouch is placed flat between the two expansion-limiting plates,
  At least one port of the pouch is connected to the gas source and the pressure-measuring means in such a way as to be able to send the pressurized gas into the pouch and to measure the pressure of the gas in the pouch,
And, in a subsequent test phase:
  The pressurized gas is sent into the pouch, with the expansion of the pouch being limited when its large walls come against the expansion-limiting plates,
Then, in a subsequent stage, the pressure drop in the pouch owing to the pressure-measuring means is compared to a predefined pressure drop threshold of a pouch that is considered intact.

If the pressure drop in the pouch is less than the threshold, it is considered that the pouch has passed the integrity check, while if the pressure drop in the pouch is greater than the threshold, it is considered that the pouch has not passed the integrity check.

Devices for implementing a checking process for filters and membranes, by the pressure drop technique, without expansion-limiting plates, for example the device SARTOCHECK® 4 of the SARTORIUS Company, are known. Devices with plates from other suppliers are known. In all of the cases, such devices are complex and bulky and difficult to ship or to use at the sites of final use of the pouches.

In contrast, an accidental rupture of the integrity of the pouch can occur after its manufacture and before its final use, for example in the phases of storage, shipping, distribution, delivery or else in the phase that immediately precedes the implementation of the pouch. This risk is all the greater the longer any of these phases lasts (for example, the storage phase can reach several years) or if it involves handling of the pouch or its contact with objects that will promote damage thereof. However, such a rupture of the integrity of the pouch cannot be decelerated by a process for checking integrity that is implemented before the integrity rupture takes place.

The documents U.S. Pat. No. 6,892,567 and U.S. Pat. No. 6,196,056 describe processes and devices for determining the integrity of a package or a compartment resting on the transmission of a test gas through the package or the wall of the compartment. This device and the associated measuring instruments form a complex and bulky unit having the limitations mentioned above.

The document US 2007/0220956 describes a process and a device for detecting a leak from a pouch designed for the production of a process that is biological and that contains a conductive fluid, placed in a rigid outer container, consisting of an electrically-operated leak detector. Such a process and device exhibit the same limitations mentioned above, unless they are applied in the case of a pouch that is filled with a conductive fluid and ultimately involve the presence of a rigid outer container.

The document U.S. Pat. No. 4,098,577 describes a process and an indicator for detecting the loss of integrity of transparent packaging that contains a product that is sealed in the packaging. The packaging is filled with an artificial atmosphere such as carbon dioxide or nitrogen. A pH-sensitive detector is placed in the packaging and can be seen through it. The detector changes color in the case of a loss of artificial atmosphere as a result of a loss of integrity of the packaging. In the embodiments considered by the document U.S. Pat. No. 4,098,577, the packaging is rigid, the product is a solid object, and the detector is moved away from the latter. The process according to the document U.S. Pat. No. 4,098,577 is unsuitable in the case of packaging that is designed to accommodate a fluid product coming into contact with the detector. In addition, the document U.S. Pat. No. 4,098,577 neither describes nor suggests, indeed quite the contrary, that the detection takes place before the product is placed in the packaging.

The document U.S. Pat. No. 4,813,541 describes a process and packaging with a tamper-proof indicator. The packaging comprises a first hermetically sealed, rigid, inner container filled with a first atmosphere and containing a substance, and a second hermetically sealed, rigid, outer container in which there is located—in a spaced position owing to crosspieces—the first container, the inner cavity of the second container outside of the first container being filled with a second atmosphere at a pressure that is different from that of the first atmosphere, and detection means being placed in the cavity and being sensitive to a modification of the second atmosphere due to a rupture of integrity of the first container or the second container. The document U.S. Pat. No. 4,813,541, which describes a very particular structure, does not suggest that the detection take place before the substance is placed in the first container.

The document WO 01/04624 describes a colorimetric system that comprises a detector that is sensitive to carbon dioxide.

The document WO96/12659 describes a so-called tamper-proof packaging that comprises an inner membrane that delimits an inner compartment, which contains a first medium that consists of air, as well as an outer membrane that delimits an outer compartment that surrounds the inner compartment and contains a second medium that consists of carbon dioxide. An indicator tab, sensitive to the surrounding environment, is provided inside the outer compartment, and it can give an indication relative to a change in the first medium and in the second medium.

The document U.S. Pat. No. 4,434,893 describes a packaging for accommodating products that comprise inner and outer cases. In one embodiment, the inner case and the outer case respectively have only a single flexible wall, and these inner and outer cases are pressurized using a gas that has a pressure that is higher than the atmospheric pressure in such a way as to inflate their flexible wall. In another embodiment, the two walls of each of the inner and outer cases are flexible. The products—capsules, gel capsules or the like—to be protected are included inside the inner case, and the inner case is itself located in this outer case in such a way as to form a protection preventing access to the products.

The document U.S. Pat. No. 4,436,203 describes a packaging that comprises an inner container of predefined size, filled with a product and pressurized before being arranged inside an outer container. After its inner pressure has dropped below the atmospheric pressure, said outer container is closed. Thus, when one of the walls of the packaging is pierced, the consumer is alerted because the product may have been touched.

The document FR 2 252 619 describes a device that is designed to be used with a packaging that is normally closed hermetically. It comprises a detector that is arranged in such a way that it is in communication with the interior of the packaging but also visible from the outside. This detector contains a pH-sensitive dye, which has a first color at a normal atmospheric pH and a second color at a pH that is slightly greater than or less than the normal atmospheric pH.

The invention therefore has as its object to eliminate the above-mentioned problems by proposing to detect the rupture of integrity of a pouch—at any desired time after its manufacture and in any case just before its use by installation in the pouch of contents that can be fluid and that come into contact with the inner surface of the pouch—in a reliable, easy and quick way, without the necessity for a heavy or complex dedicated device, or difficult or delicate operations, without the necessity of having to resort to specialized personnel especially and exclusively dedicated to checking the integrity, and without the necessity of having to test the pouch positively to ensure its integrity, the loss of integrity being revealed automatically and therefore without the necessity, when the pouch is part of a large number of pouches, of having to test each pouch positively.

BRIEF SUMMARY OF THE INVENTION

For this purpose, according to a first aspect, the purpose of the invention is a pouch with an incorporated loss of integrity indicator that is active per se and after the manufacturing of the pouch and at least before the time when a biopharmaceutical product or device is to be introduced thereinto, Comprising:
A first flexible, closed, inner casing, made of at least one non-porous plastic material with a high-capacity gas barrier, delimiting a first space, forming a pouch stricto sensu that can accommodate the biopharmaceutical product or device when desired but devoid of the latter, comprising, on the one hand, first introduction means for the purpose of subsequent introduction, when desired, of the biopharmaceutical product or device into the pouch stricto sensu, and, on the other hand, first evacuation means for the purpose of subsequent evacuation, when desired, of the biopharmaceutical product or device of the pouch stricto sensu, with the first introduction means and the first evacuation means being in the inactive closed state, A second closed, outer casing made of at least one non-porous plastic material with a high-capacity gas barrier, delimiting a second space in which the pouch stricto sensu is located for the purpose of the detection of a possible loss of integrity of the latter, comprising, on the one hand, second introduction means that made possible the preliminary introduction of the pouch stricto sensu in the second space, and, on the other hand, second evacuation means for the purpose of the evacuation of the pouch stricto sensu from the second space, the second introduction means and the second evacuation means being in the inactive closed state, Spacer means (11) interposed between the pouch stricto sensu and the second casing, where it is ensured that the inner surface of the second casing does not conceal any zone of possible loss of integrity of the outer surface of the pouch stricto sensu, At least one selected tracer gas that is located, respectively, in the first space or in the second space, with a higher partial pressure than in the second space or in the first space, At least one colorimetric detector of at least one tracer gas that is responsive to the concentration of at least one tracer gas in the environment in which it is located, by switching from a first color to a second color that is different from the first color, with the at least one colorimetric detector being located, respectively, in the second space or in the first space, In such a way as to be able, at any desired time after the pouch is manufactured and at least just before the time when the pouch stricto sensu is to be evacuated from the second casing and the biopharmaceutical product or device is to be introduced into the pouch stricto sensu, to interpret the visual assessment that the at least one colorimetric detector is either of the first color, signifying that the pouch stricto sensu has kept its integrity, or of the second color, signifying that the pouch stricto sensu has lost its integrity.

According to a first possible embodiment, at least one colorimetric detector is housed in the first space that forms the pouch stricto sensu, with the second space—outside of the pouch stricto sensu—having an environment that comprises the tracer gas at a higher partial pressure than the environment of the first space. In this case, according to a variant embodiment, at least one colorimetric detector that is housed in the first space forming the pouch stricto sensu and the biopharmaceutical product or device designed to to fill the pouch stricto sensu are of such natures that they can be in reciprocal contact without the biopharmaceutical quality of the product or device that will be placed there subsequently being thereby affected. According to another variant embodiment, the pouch with an incorporated and active loss of integrity indicator comprises at least one separation wall that is located in the first space that forms the pouch stricto sensu, having a selective permeability, namely allowing the tracer gas to pass and not allowing the biopharmaceutical product or device to pass, whereby this at least one separation wall delimits by itself or with the first casing at least a first compartment in which the at least one colorimetric detector is housed.

According to a second possible embodiment, at least one colorimetric detector is housed in the second space, outside of the pouch stricto sensu, with the first space that forms the pouch stricto sensu having an environment that comprises the tracer gas at a higher partial pressure than the environment of the second space outside of the pouch stricto sensu. According to a variant embodiment, the pouch comprises at least one separation wall that is located in the second space outside of the pouch stricto sensu that delimits by itself or with the first or the second casing at least one second compartment in which the at least one colorimetric detector is housed.

According to the embodiments, the pouch stricto sensu is a 2D pouch or a 3D pouch that comprises at least one gusset.

According to one embodiment, the spacer means (11) are porous material or comprise porous material. For example, they come in the form of at least one porous layer or at least one porous material. According to a variant embodiment, they come in the form of at least one porous layer or at least one porous material that structurally or functionally integrally covers the outer surface of the pouch stricto sensu, with the first means for introduction and the first means for evacuation of the pouch stricto sensu being in the inactive closed state, and the outer surface of the interior of the gusset of the pouch stricto sensu, when a 3D pouch is involved.

According to the embodiments, the at least one colorimetric detector is arranged in a non-fixed or fixed manner in the space—first or second space—in which it is located, then being, in a variant embodiment, fixed or incorporated in the inner surface of the first casing, in the inner surface of the second casing, or with spacer means (11).

According to the embodiments, the first casing, on the one hand, and the second casing, on the other hand, comprise one or more integral superposed layers and incorporate at least one plastic material with a high-capacity gas barrier.

According to the embodiments, a tracer gas is selected from the group that comprises oxygen, carbon dioxide, and helium.

According to one embodiment, the at least one colorimetric detector is an autonomous element, lacking an internal energy source and outside connections.

According to one embodiment, the at least one colorimetric detector has a large surface, so as to ensure simultaneously that it is responsive to the tracer gas concentration in the environment in which it is located and that an observer can note visually if it has the first color or the second color.

According to one embodiment, the at least one colorimetric detector is at a localized site in the pouch.

According to one embodiment, the pouch with an incorporated and active loss of integrity indicator comprises several colorimetric detectors at several sites in the pouch. In a variant embodiment, the colorimetric detectors are at least essentially distributed in the pouch. According to a first embodiment, the pouch comprises several colorimetric detectors that are analogous in the same space, first space or second space outside of the pouch stricto sensu. According to a second embodiment, the pouch with an incorporated and active loss of integrity indicator first comprises, on the one hand, at least one first colorimetric detector that is responsive to the concentration of a first tracer gas, and, on the other hand, at least one second colorimetric detector that is responsive to the concentration of a second first tracer gas that is different from the first tracer gas, and, secondly, on the one hand, a first tracer gas in the second space with a higher partial pressure than in the first space, and, on the other hand, a second tracer gas in the first space with a higher partial pressure than in the second space outside of the pouch stricto sensu.

According to one embodiment, a space—first or second space outside of the pouch stricto sensu—contains tracer gas, and the other space—second space outside of the pouch stricto sensu or first space—does not comprise or substantially does not comprise tracer gas.

According to one embodiment, a colorimetric detector is generally flat, planar or curved, such as a pellet or a pseudo-pellet, or generally a line or a strip, while being rigid, flexible, or semi-flexible semi-rigid.

According to one embodiment, the pouch with an incorporated and active loss of integrity indicator is flattened or essentially flattened on itself and thus easily suitable for storage, for shipping, or for handling.

According to one characteristic, the second outer casing is able to allow an outside observer to identify—from outside of the outer casing—the color of at least one colorimetric detector. According to a variant embodiment, the second outer casing is transparent or translucent or comprises a transparent or translucent window for observing the color of at least one colorimetric detector that is located opposite or in the vicinity.

According to one embodiment, the second casing is flexible.

According to one embodiment, the pouch with an incorporated and active loss of integrity indicator also comprises an outer protective packaging in which the second casing, in which the pouch stricto sensu is located, is housed.

According to a second aspect, the purpose of the invention is the application of a pouch with an incorporated and active loss of integrity indicator as it was just described, in which, just before the time when the pouch stricto sensu is evacuated from the second casing and the biopharmaceutical product or device is introduced into the pouch stricto sensu, the at least one colorimetric detector is being of the first color, consisting in opening the second evacuation means of the second casing, to evacuate, extract, or remove the pouch stricto sensu from the second space, to open the first means for introducing the pouch stricto sensu and to introduce the biopharmaceutical product or device into the first space, so as to provide a pouch stricto sensu that has all of its integrity containing the biopharmaceutical product or device, which pouch stricto sensu and the biopharmaceutical product or device that it contains then being suitable for use.

According to a third aspect, the purpose of the invention is a pouch stricto sensu that has its full guarantee of integrity, specially designed to contain a biopharmaceutical product or device, created from a pouch with an incorporated and active loss of integrity indicator as it was just described, in which, with the at least one colorimeteric detector being of the first color, the pouch stricto sensu was evacuated, extracted, or removed from the second casing, with the pouch stricto sensu then being suitable for use.

According to a possible variant embodiment, at least one colorimetric detector is housed in the first space of the pouch stricto sensu.

According to a fourth aspect, the purpose of the invention is a process for the production of a pouch with an incorporated and active loss of integrity indicator as it was described, in which:

A first flexible casing, made of at least one non-porous plastic material with a high-capacity gas barrier, delimiting a first space, forming a pouch stricto sensu that can accommodate the biopharmaceutical product or device when desired but devoid of the latter, comprising, on the one hand, first introduction means for the purpose of subsequent introduction, when desired, of the biopharmaceutical product or device into the pouch stricto sensu, and, on the other hand, first evacuation means for the purpose of subsequent evacuation, when desired, of the biopharmaceutical product or device of the pouch stricto sensu, is provided, A second casing made of at least one non-porous plastic material with a high-capacity gas barrier, comprising, on the one hand, second introduction means for the purpose of introducing the pouch stricto sensu into the second space, and, on the other hand, second evacuation means for the purpose of the evacuation of the pouch stricto sensu from the second space, is provided, Spacer means (11) are provided, At least one selected tracer gas is provided, At least one colorimetric detector of at least one tracer gas that is responsive to the concentration of at least one tracer gas in the environment in which it is located, by switching from a first color to a second color that is different from the first color, is provided, The pouch stricto sensu is introduced into the second casing, and spacer means (11) are interposed between them in such a way that the inner surface of the second casing does not conceal any zone of possible loss of integrity of the outer surface of the pouch stricto sensu, The at least one selected tracer gas is introduced, respectively, into the first space or into the second space outside of the pouch stricto sensu, with a higher partial pressure than in the second space outside of the pouch stricto sensu or in the first space, and the at least one colorimetric detector of the at least one tracer gas is placed in the second space outside of the pouch stricto sensu or in the first space, respectively, And, finally, the pouch stricto sensu and the second casing are closed.

According to the embodiments, the at least one colorimetric detector is provided in the pouch stricto sensu, and the at least one tracer gas is introduced into the second space outside of the pouch stricto sensu at a higher partial pressure than the environment of the first space, and the at least one colorimetric detector is provided in the second casing outside of the pouch stricto sensu, and the at least one tracer gas is introduced into the pouch stricto sensu at a higher partial pressure than the environment of the first space.

According to one embodiment, the at least one tracer gas is introduced into a space—first space or second space outside of the pouch stricto sensu—and the at least one tracer gas is not introduced without the other space—second space outside of the pouch stricto sensu or first space.

According to one embodiment, air is purged from the space that contains tracer gas at a lower partial pressure or without tracer gas.

According to the embodiments, the at least one colorimetric detector is provided in a non-fixed way in the space—first or second space—in which it should be located or in contrast in a fixed way in the space—first or second space—in which it should be located, by fixing it or incorporating it in the inner surface of the first casing, in the inner surface of the second casing, or in the spacer means.

According to one embodiment, several colorimetric detectors are placed at several sites in the pouch. According to one variant embodiment, several analogous colorimetric detectors are placed in the same space, first space, or second space outside of the pouch stricto sensu. According to another variant embodiment, at least one colorimetric detector is placed in the first space, and at least one colorimetric detector is placed in the second space outside of the pouch stricto sensu.

According to one embodiment, the second casing in which the pouch stricto sensu is located is placed in an outer protective packaging.

According to a fifth and final aspect, the purpose of the invention is a process relative to pouches stricto sensu that is specially designed to contain a biopharmaceutical product or device and having to exhibit its full guarantee of integrity, with the process comprising, on a manufacturing site, initial operations that consist in manufacturing the pouch stricto sensu, on a site of use, of final operations that consist in using the pouch stricto sensu by placing there, when desired, the biopharmaceutical product or device and by ensuring the desired treatment, and intermediate operations of storage, shipping, and handling, characterized by:

The production, on the manufacturing site, of a pouch with an incorporated and active loss of integrity indicator that comprises the pouch stricto sensu, as it was described, The shipping of the pouch with an incorporated and active loss of integrity indicator that comprises the pouch stricto sensu from the manufacturing site to the site of use, by means of, if necessary, operations of storage and handling, And, at least on the site of use and just before the time when the pouch stricto sensu is evacuated from the second casing and the biopharmaceutical product or device is introduced into the pouch stricto sensu, the visual examination of the color of the at least one colorimetric detector so as to note whether the at least one colorimetric detector is of the first color or of the second color, with the pouch stricto sensu being used for the biopharmaceutical product or device only if the at least one colorimetric detector is of the first color, while if the at least one colorimetric detector is of the second color, the pouch stricto sensu is not used for the biopharmaceutical product or device.

According to one characteristic of this process, there is a stage in which the colorimetric detector keeps the first color or switches from the first color to the second color that occurs in the background during the intermediate operations of storage, shipping, and handling.

BRIEF DESCRIPTION OF THE DRAWINGS

Several embodiments of the invention will now be described using drawings, in which:

FIGS. 4 and 5 are two views that are analogous to FIGS. 2 and 3 of a second embodiment of a pouch with an incorporated and active loss of integrity indicator; in this second embodiment, the colorimetric detector is housed in the second space that is delimited by the second casing, outside of the pouch stricto sensu;

FIGS. 6 and 7 are two views that are analogous to FIGS. 2 and 4 and two other embodiments of a pouch with an incorporated and active loss of integrity indicator, comprising several colorimetric detectors, respectively in the second space that is delimited by the second casing, outside of the pouch stricto sensu and at the same time in the second space that is delimited by the second casing, outside of the pouch stricto sensu and in the pouch stricto sensu.

DETAILED DESCRIPTION OF THE PREFERRED EMBODIMENTS

Figure 1A:
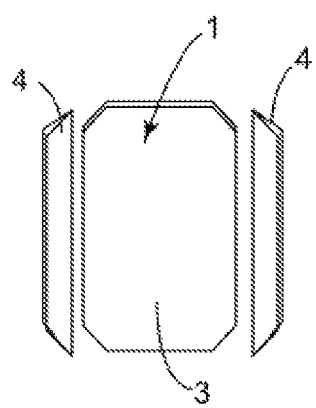
FIGS. 1A, 1B and 1C are three views of a 3D-type pouch stricto sensu, namely, respectively, an exploded and diagrammatic view of the pouch before production, an elevation view of the pouch folded flat, and a perspective view of the pouch by volume.
Figure 1B:
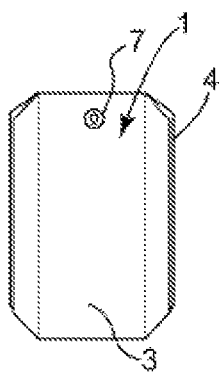
Figure 1C:
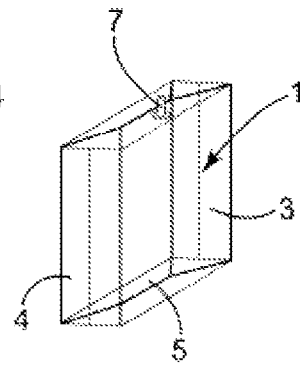

Flexible 3D pouches 1, specially designed to contain a biopharmaceutical fluid as defined above, are known in the biopharmaceutical field.

Such a pouch 1 is called "pouch stricto sensu" here, meaning by this expression that it constitutes per se the pouch that is designed to contain biopharmaceutical fluid, whereas this pouch stricto sensu is incorporated in a more complex unit called "pouch with an incorporated and active loss of integrity indicator" 2.

Such a pouch stricto sensu 1 can have a large volume of at least 50 liters, up to 1,000 liters, and even more, which means that it is described as 3D. Such a pouch is described in, for example, the International Application WO00/04131, whereby this embodiment does not exclude others. Such a pouch is also marketed by the Sartorius Company under the trademark FLEXEL® 3D.

Such a pouch stricto sensu 1 comprises in particular primary walls 3 and two side gussets 4, with the different constituent parts being welded to one another along seam lines 5 in such a way as to form a casing, called "first casing," also designated by the reference 1.

The pouch stricto sensu 1 is closed, flexible and made from non-porous plastic material with a high-capacity gas barrier, comprising one or more integral superposed layers that incorporate at least one plastic material with a high-capacity gas barrier, such as EVOH.

The pouch stricto sensu 1 delimits a first space 6, of suitable volume, able to accommodate the biopharmaceutical product when this is desired.

The pouch stricto sensu 1 comprises first introduction means 7 for the purpose of the introduction, when this is desired, of the biopharmaceutical product into the first space 6.

The pouch stricto sensu 1 also comprises first evacuation means for the purpose of the evacuation, when this is desired, of the biopharmaceutical product of the first space 6.

Such first introduction means and first evacuation means can come in the form of ports, arranged to be open or closed, based on requirements.

Such a pouch stricto sensu 1 is typically found in two end states: a state that is folded flat and a state that is deployed unfolded. It can be deformed to switch from one to the other of these states or is found in any intermediate state.

Such a pouch stricto sensu 1 is typically designed to be combined with a rigid container that contains the pouch from the outside. Such a container is described in a possible variable embodiment in the document EP-A-1012073 and also marketed by the Sartorius Company under the trademark PALLETTANK®.

Such a pouch stricto sensu 1 is typically designed to be combined with a rigid container.

The operating process of such pouches stricto sensu 1 consists, on a given manufacturing site, in implementing initial operations that consist in manufacturing the pouch stricto sensu 1 and, on a site of use, most often different and distant from the manufacturing site, in producing a certain number of so-called final operations that consist in using the pouch stricto sensu 1, i.e., placing there, at the time when this is desired, a biopharmaceutical product, and then by ensuring the desired treatment. This treatment is storage, shipping, or any other functional treatment such as mixing, aeration, or the like.

Between the initial operations and the final operations, intermediate operations, such as, typically, storage, shipping or handling, take place. These intermediate operations can extend over a rather long period, for example several months, and even several years, involving, for example, storage.

Although the pouches stricto sensu 1 are produced from non-porous plastic material with a high-capacity gas barrier and although the seam lines 5 are a priori airtight, it is essential to ensure that each pouch has the desired seal, not only during its manufacturing, but also, after manufacturing, at least just before the time when the biopharmaceutical product is introduced thereinto. Failing this, the quality of the biopharmaceutical product could be affected and the biopharmaceutical product made unusable, or the pouch stricto sensu could be so deteriorated that it could not perform its function. Such situations are particularly serious and troublesome, whereas the biopharmaceutical product that is placed in the pouch stricto sensu is expensive and rare in large amounts.

A pouch stricto sensu 1 whose possession of the desired seal has been verified is called a pouch stricto sensu 1 that has its full guarantee of integrity. A pouch that does not have the desired seal is called a pouch stricto sensu 1 that has lost its integrity.

The integrity of the pouch stricto sensu 1 is essential so that the latter performs its function as an airtight and sterile container, maintaining the sterility being a critical factor in the biopharmaceutical processes.

The integrity of a pouch stricto sensu 1 can be affected as a result of manufacturing defects (presence of one or more small holes in the pouch or deficient seam lines 5, for example) or as a result during intermediate operations of storage, shipping or handling, with the risk being higher as these intermediate operations extend over a long period of time.

So as to be able, at least on the site of use and just before the time provided, to introduce the biopharmaceutical product into the pouch stricto sensu 1, the process relative to the pouches stricto sensu is modified, in accordance with the invention.

This process first comprises the production, on the manufacturing site, of a pouch stricto sensu and the manufacturing, starting from the latter, of a pouch with an incorporated and active loss of integrity indicator 2.

This process next comprises the shipping of this pouch with an incorporated and active loss of integrity indicator 2 from the manufacturing site to the site of use, by means of, if necessary, operations of storage and handling, all of these operations constituting the so-called intermediate operations.

This process finally comprises—at least on the site of use and just before the time when the biopharmaceutical product is introduced into the pouch stricto sensu 1—the checking of the integrity of the pouch stricto sensu 1, the latter being used for the biopharmaceutical product only if the integrity is guaranteed, while if the integrity cannot be guaranteed, the pouch stricto sensu 1 is not used for the biopharmaceutical product.

According to the invention, this checking of the integrity of the pouch stricto sensu 1 is achieved in a reliable, easy and quick way, without the necessity for a heavy or complex dedicated device, or difficult or delicate operations, without the necessity for having recourse to specialized personnel, especially and exclusively dedicated to checking the integrity, and without the necessity for having to test the pouch positively for ensuring its integrity, with the loss of integrity being revealed automatically, and therefore without the necessity—when the pouch is part of a large number of pouches—of having to test each pouch positively.

In addition, this checking is carried out after an operating phase that takes place in the background during the intermediate operations of storage, shipping, and handling, and without the necessity for intervention.

The invention applies not only in the case where the pouch stricto sensu 1 is a 3D pouch, but also in the case of a 2D pouch.

The invention also applies not only in the case of a biopharmaceutical product, but also in the case of a biopharmaceutical device, as defined above.

The pouch 2 with an incorporated loss of integrity indicator, that is active per se—and after the manufacturing of the pouch and at least before the time when a biopharmaceutical product or device is introduced thereinto, as it is manufactured, and before all use—first of all comprises the pouch stricto sensu 1.

The pouch stricto sensu 1 is then closed and devoid of a biopharmaceutical product or device. Its first introduction means 7 and its first evacuation means are in the inactive closed state.

The pouch 2 with an incorporated and active loss of integrity indicator next comprises a second outer casing 8, with the pouch stricto sensu 1 being inside.

The second casing 8 is closed, produced from at least one non-porous plastic material with a high-capacity gas barrier, and, in the embodiment shown, flexible. For example, the second casing 8 comprises one or more integral superposed layers that incorporate at least one plastic material with a high-capacity gas barrier, such as EVOH.

The second casing 8 delimits a second space 9, in which the pouch stricto sensu 1 is located.

It is by this arrangement that the pouch 2 makes possible the detection of a possible loss of integrity of the pouch stricto sensu 1.

The second casing 8 also comprises second introduction means 10 having allowed the preliminary introduction of the pouch stricto sensu 1 into the second space 9, such as an opening that is next closed by a seam line.

The second casing 8 also comprises second evacuation means (extraction or removal) for the purpose of the evacuation (extraction or removal) of the pouch stricto sensu 1 from the second space 9, such as a tearing of the second casing 8.

In the pouch 2 with an incorporated and active loss of integrity indicator, the second introduction means 10 and the second evacuation means are in the inactive closed state.

The pouch 2 with an incorporated and active loss of integrity indicator next comprises spacer means 11, interposed between the stricto sensu pouch 1 and the second casing 8.

These spacer means 11 are where it is ensured that the inner surface 8a of the second casing 8 does not conceal any zone of possible loss of integrity of the outer surface 1a of the pouch stricto sensu 1.

The pouch 2 with an incorporated and active loss of integrity indicator next comprises at least one selected tracer gas, and at least one colorimetric detector 12 of this tracer gas.

Such a colorimetric detector 12 is responsive to the concentration of the tracer gas in the environment in which it is located, by switching from a first color to a second color that is different from the first color.

Such a tracer gas is selected from, for example, the group that comprises oxygen, carbon dioxide, and helium. Such a colorimetric detector 12 that is adapted to such a tracer gas is accessible to one skilled in the art. Such a colorimetric detector 12 is an autonomous element, lacking any internal energy source and outside connections.

Such a colorimetric detector 12 has a large surface, so as to ensure simultaneously that it is effectively responsive to the tracer gas concentration in the environment in which it is located and to make it possible for an observer to be able to visually note if it has the first color or the second color.

According to the embodiments, such a colorimetric detector 12 is generally flat, planar or curved, such as a pellet or a pseudo-pellet, or generally a line or a strip, while being rigid, flexible, or semi-flexible semi-rigid.

The pouch 2 with an incorporated and active loss of integrity indicator next comprises spacer means, is flattened or essentially flattened on itself, and thus is easily suitable for storage, for shipping, or for handling, in particular in the operations that are described as intermediate operations above.

In general, the tracer gas is respectively in the first space 6 or in the second space 9 outside of the pouch stricto sensu 1, with a higher partial pressure than in the second space 9 outside of the pouch stricto sensu 1 or in the first space 6. As a variant, a space—first or second space outside of the pouch stricto sensu 6, 9—contains tracer gas, and the other space—second space outside of the pouch stricto sensu or first space 9, 6—does not comprise or substantially does not comprise tracer gas.

Whereas the tracer gas is respectively in the first space 6 or in the second space 9 outside of the pouch stricto sensu 1, the colorimetric detector 12 is respectively located in the second space 9 outside of the pouch stricto sensu 1 or in the first space 6.

Thus, at any time desired after the manufacturing of the pouch 2 with an incorporated and active loss of integrity indicator—and at least just before the time when the pouch stricto sensu 1 is used (introduction of the biopharmaceutical product or device into the pouch stricto sensu 1)—an outside observer can note de visu the color of the colorimetric detector 1.

This observer interprets this visual assessment in the following manner: if the colorimetric detector 12 is of the first color, the pouch stricto sensu 1 has all of its integrity. If the colorimetric detector 12 is of the second color, the pouch stricto sensu 1 has lost its integrity.

"Interpreting" is defined as the fact of providing for the pouch stricto sensu 1, relative to its integrity, a meaning that originates from the assessment of the color of the colorimetric detector 12. This correspondence of the color of the colorimetric detector 12 ⇔ integrity of the pouch stricto sensu 1 is one-to-one, which leaves no doubt as to whether the pouch stricto sensu 1 has integrity or not, in the sole view of the color of the colorimetric detector 12, without the necessity for operations, handling, computations, calculations, . . . .

The second casing 8 is designed in such a way as to make it possible for an outside observer to identify—from the outside of this casing 8—the color of the colorimetric detector 12 that is located inside. For this purpose, the second casing 8 is, according to the embodiments, transparent or translucent, or it comprises a transparent or translucent window for observing the color of the colorimetric detector 12 that is located opposite to or in the vicinity of this window.

According to one possible embodiment, an outer protective packaging in which the pouch 2 with an incorporated and active loss of integrity indicator is housed is provided, it being understood that the second casing 8 can itself be a part of the packaging and the protection of the pouch stricto sensu 1.

Figure 2:
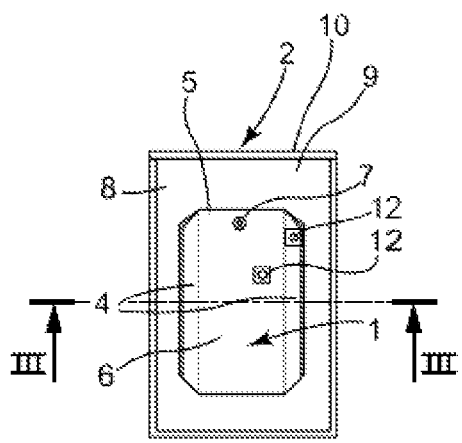
FIGS. 2 and 3 are two views of a first embodiment of the pouch with an incorporated loss of integrity indicator that is active per se and after the manufacturing of the pouch and at least before the time when a biopharmaceutical product or device is introduced therein, comprising a pouch stricto sensu, a second outer casing, spacer means, a tracer gas, and a colorimetric detector of the tracer gas, namely an elevation view and a cutaway view through a transverse plane, along the line III-III of FIG. 2; in this first embodiment, the colorimetric detector is housed in the pouch stricto sensu.
Figure 3:
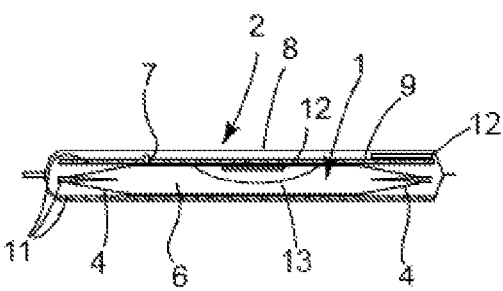

In a first embodiment that is illustrated by FIGS. 2 and 3, the colorimetric detector 12 is housed in the first space 6 that forms the pouch stricto sensu 1, while the second space 9 outside of the pouch stricto sensu 1 has an environment that comprises the tracer gas at a higher partial pressure than the environment of the first space 6.

According to a first variant of this first embodiment, the colorimetric detector 12 and the biopharmaceutical product or device are of such natures that they can be in reciprocal contact without the biopharmaceutical quality of the product or device being thereby affected.

According to a first variant of this same first embodiment, the pouch 2 comprises a separation wall located in the first space 6 that forms the pouch stricto sensu 1. This separation wall has a selective permeability, namely allowing the tracer gas to pass and not allowing the biopharmaceutical product or device to pass. This separation wall delimits, by itself alone or in combination with the first casing 1, a first compartment in which the colorimetric detector 12 is housed.

In a second embodiment that is illustrated by FIGS. 4 and 5, the colorimetric detector 12 is housed in the second space 9, outside of the pouch stricto sensu 1, with the first space 6 then having an environment that comprises the tracer gas at a higher partial pressure than the environment of the second space 9, outside of the pouch stricto sensu 1.

According to a variant of this second embodiment, the pouch 2 comprises—outside of the pouch stricto sensu 1—a separation wall that is located in the second space 9, outside of the pouch stricto sensu 1. This separation wall delimits—by itself alone or in combination with the first casing 1 or with the second casing 8—a second compartment in which the colorimetric detector 12 is housed.

According to one embodiment, the spacer means 11 are or comprise porous material. For example, they come in the form of at least one porous layer or at least one porous material, structurally or functionally integrally covering the outer surface 1a of the pouch stricto sensu 1. According to the embodiments, such a porous layer or at least one porous material is produced in fabrics, in non-woven fabrics, in PE, in PP, in PTFE, or the like, whereby this list is not limiting. The purpose of the construction arrangement that is indicated is that the lower surface 8a of the second casing 8, even if it is against the outer surface 1a of the first casing 1, does not conceal any zone of possible loss of integrity of the pouch stricto sensu 1, with the porous layer or at least one porous material of the space means 11 being interposed between these two surfaces 1a and 8a.

In addition, the spacer means 11, thus produced, structurally or functionally integrally cover the first introduction means 7 and the first evacuation means of the pouch stricto sensu 1, being in the inactive closed state.

Also, the spacer means 11, thus produced, structurally or functionally integrally cover the outer surface of the interior of the gusset 4 of the pouch stricto sensu 1 when the latter is a 3D pouch.

Structural integral covering is defined as the fact that the spacer means 11 structurally integrally cover the pouch stricto sensu 1. Functional integral covering is defined as the fact that the spacer means 11, without necessarily integrally and structurally covering the pouch stricto sensu 1, ensure the spacing function over the entire surface of the pouch stricto sensu 1.

The pouch 2 with an incorporated and active loss of integrity indicator can be the object of various variant embodiments.

According to the embodiments, the colorimetric detector 12 is arranged in a non-fixed or, in contrast, a fixed way in the space—first space 6 or second space 9—in which it is located. In the second case, the colorimetric detector 12 is, for example, fixed or incorporated in the inner surface 1b of the first casing 1, or in the inner surface 8a of the second casing 8, or else in the spacer means 11.

According to the embodiments, the colorimetric detector 12 is at a localized site in the pouch 2 with an incorporated and active loss of integrity indicator or else several colorimetric detectors 12 are provided at several sites in the pouch 2, in particular at least essentially distributed in the pouch in such a way as to be located close enough for any possible loss of integrity, with such a structure providing maximum safety and efficiency.

For example, several analogous colorimetric detectors 12 can be provided in the same space, namely the first space 1 or the second space 9 outside of the pouch stricto sensu 1, as it is shown in FIG. 6.

Or, there may be provided one (or more) first colorimetric detector(s) 12a located in the first space 1 and one (or more) second colorimetric detector(s) 12b located in the second space 9 outside of the pouch stricto sensu 1, as it is shown in FIG. 7. In such an embodiment, the first detector 12a is responsive to a first tracer gas, and the second detector 12b is responsive to a second tracer gas, with these two tracer gases being, of course, different.

A pouch 2 with an incorporated and active loss of integrity indicator is implemented in the following manner: just before the time when the pouch stricto sensu 1 is evacuated, extracted, or removed from the second casing 8 and the biopharmaceutical product or device is introduced into the pouch stricto sensu 1, with the colorimetric detector 12 being of the first color, which means that the pouch stricto sensu 1 has all of its integrity, the second evacuation means of the second casing 8 are opened, the pouch stricto sensu 1 is evacuated, extracted, or removed from the second space 9, the first introduction means 7 of the pouch stricto sensu 1 are opened, and the biopharmaceutical product or device is introduced into the first space 1. Thus, a pouch stricto sensu 1 that has all of its integrity and that contains the biopharmaceutical product or device is provided. This pouch stricto sensu 1 and the biopharmaceutical product or device that it contains are then suitable for the desired use.

In the case where the colorimetric detector 1 is housed in the pouch stricto sensu 1, this pouch stricto sensu 1 that results from the implementation of the pouch 2 with an incorporated and active loss of integrity indicator comprises the colorimetric detector 12 in question, with the latter being of the first color. As indicated above, the pouch stricto sensu 1 has been evacuated, extracted, or removed from the second casing 8 and is then suitable for use.

The process for production of a pouch 2 with an incorporated and active loss of integrity indicator is as follows.

First of all, a first casing 1 that is devoid of biopharmaceutical product or device, a second casing 8, spacer means 11, tracer gas, and a colorimetric detector 12 corresponding to the tracer gas are provided.

Then, the pouch stricto sensu 1 is introduced into the second casing 8, and the spacer means 11 are interposed between them as disclosed.

Also, the tracer gas is introduced into the space 6 or 9 outside of the pouch stricto sensu 1 before accommodating it, and the colorimetric detector 12 is placed in the other space 9 outside of the pouch stricto sensu 1 or 6.

Finally, the pouch stricto sensu 1 and the second casing 8 are closed.

This process may be the object of different variant embodiments that correspond to the variants of the pouch 2.

Thus, according to the embodiments, the colorimetric detector 12 is provided in the pouch stricto sensu 1, and the tracer gas is introduced into the second space 9 outside of the pouch stricto sensu 1 at a higher partial pressure than the environment of the first space 1, or, conversely, the colorimetric detector 12 is provided in the second casing 8, outside of the pouch stricto sensu 1, and the tracer gas is introduced into the pouch stricto sensu 1 at a higher partial pressure than the environment of the second space 9, outside of the pouch stricto sensu 1.

According to one embodiment, the tracer gas is introduced into a space—first space 6 or second space 9 outside of the pouch stricto sensu 1, and the tracer gas is not introduced into the other space—second space 9 outside of the pouch stricto sensu 1 or first space 6.

According to one embodiment, the air is purged from the space 6, 9 containing the tracer gas at a lower partial pressure or without tracer gas.

According to the embodiments, the colorimetric detector 12 is provided in the space—first or second space outside of the pouch stricto sensu 6 or 9—in which it is to be located, in a non-fixed way or, in contrast, a fixed way, for example by fixing it or by incorporating it in the inner surface 1a of the first casing 1, in the inner surface 8a of the second casing 8, or in the spacer means 11.

According to one embodiment, several colorimetric detectors 12 are placed at several sites in the pouch 2, namely several analogous colorimetric detectors in the same space, first space 6 or second space 9 outside of the pouch stricto sensu 1, or a first colorimetric detector 12a in the first space 6 and a second colorimetric detector 12b in the second space 9 outside of the pouch stricto sensu 1.

Also, according to one embodiment, the process comprises a stage in which the second casing 8, in which the pouch stricto sensu 1 is located, is placed in an outer protective packaging.

The operating process is therefore such that it comprises the following stages:
  The production, on the manufacturing site, of a pouch 2 with an incorporated and active loss of integrity indicator that comprises the pouch stricto sensu 1,
  The shipping of the pouch 2 from the manufacturing site to the site of use, by means of, if necessary, operations of storage and handling,
  And, at least on the site of use and just before the time when the pouch stricto sensu 1 is evacuated, extracted, or removed from the second casing 8 and the biopharmaceutical product or device is introduced into the pouch stricto sensu 1, the visual examination by the outside observer of the color of the colorimetric detector 12 so as to note whether it is of the first color or the second color. The pouch stricto sensu 1 is used for the biopharmaceutical product or device only if the colorimetric detector 12 is of the first color, while if the colorimetric detector 12 is of the second color, the pouch stricto sensu 1 is not used for the biopharmaceutical product or device.

The colorimetric detector 12 keeps the first color or switches from the first color to the second color in the background during the intermediate operations of storage, shipping, and handling.

The invention claimed is:

1. A pouch comprising:
  a first flexible, closed, inner casing made of at least one non-porous plastic material with a high-capacity gas barrier, delimiting a first space, forming a first space pouch configured to accommodate a fluid biopharmaceutical product or device, the inner casing including
    a first introduction means for introducing the biopharmaceutical product or device into the first space pouch, and
    a first evacuation means for subsequently evacuating the biopharmaceutical product or device from the first space pouch, the first introduction means and the first evacuation means being in an inactive closed state;
  a second, closed, outer casing made of at least one non-porous plastic material with a high-capacity gas barrier, delimiting a second space in which the first space pouch is located for detection of a loss of integrity of the first space pouch including second introduction means for preliminarily introducing the first space pouch into the second space, and second evacuation means for evacuating the first space pouch from the second space, the second introduction means and the second evacuation means being in the inactive closed state;

a spacer means interposed between the first space pouch and the second casing, an inner surface of the second casing being configured to not conceal a zone of loss of integrity of an outer surface of the first space pouch, the spacer means being or including porous material;

at least one tracer gas that is located respectively in one of the first space or in the second space, the second space being outside of the first space pouch, having a higher partial pressure than a pressure in the other of the first space and the second space; and an incorporated loss of integrity indicator including at least one colorimetric detector that detects the at least one tracer gas, the at least one colorimetric detector being responsive to a concentration of the tracer gas in an environment in which the detector is located, by switching from a first color to a second color that is different from the first color, the at least one colorimetric detector being located in one or more of the second space outside of the first space pouch and in the first space, wherein the colorimetric detector is configured to visually indicate one of the first color, signifying that the first space pouch has kept its integrity, and the second color, signifying that the first space pouch has lost its integrity, after the pouch with the incorporated loss of integrity indicator is manufactured and at least before the time when the first space pouch is evacuated, extracted, or removed from the second casing and the biopharmaceutical product or device is introduced into the first space pouch, and the colorimetric detector is configured to detect the at least one tracer gas when the first space pouch is devoid of the biopharmaceutical product or device and when the second, closed, outer casing is maintained in a closed state.

2. The pouch with an incorporated and active loss of integrity indicator according to claim 1, wherein the at least one colorimetric detector is housed in the first space that forms the first space pouch, the second space outside of the first space pouch having an environment that includes the tracer gas at the higher partial pressure than an environment of the first space.

3. The pouch with an incorporated and active loss of integrity indicator according to claim 2, further comprising at least one separation wall that is located in the first space that forms the first space pouch, the at least one separation wall having a selective permeability allowing the tracer gas to pass and not allowing the biopharmaceutical product or device to pass, the at least one separation wall delimiting by itself or with the first casing at least a compartment in which the at least one colorimetric detector is housed.

4. The pouch with an incorporated and active loss of integrity indicator according to claim 1, wherein the at least one colorimetric detector is housed in the second space outside of the first space pouch, the first space forming the first space pouch and having an environment that includes the tracer gas at the higher partial pressure than an environment of the second space outside of the first space pouch.

5. The pouch with an incorporated and active loss of integrity indicator according to claim 4, further comprising at least one separation wall located in the second space outside of the first space pouch that delimits by itself or with one of the inner casing and the outer casing at least one compartment in which the at least one colorimetric detector is housed.

6. The pouch with an incorporated and active loss of integrity indicator according to claim 1, wherein the first space pouch is a two-dimensional pouch or a three-dimensional pouch that includes at least one gusset.

7. The pouch with an incorporated and active loss of integrity indicator according to claim 1, wherein the spacer means comprises at least one porous material made of one or more of fabrics, non-woven fabric, polyethylene (PE), polypropylene (PP), polytetrafluoroethylene (PTFE).

8. The pouch with an incorporated and active loss of integrity indicator according to claim 6, wherein the at least one porous material structurally or functionally integrally covers the outer surface of the first space pouch.

9. The pouch with an incorporated and active loss of integrity indicator according to claim 8, wherein the spacer means structurally or functionally integrally covers the outer surface of an interior of a gusset of the first space pouch, the pouch being a three-dimensional pouch.

10. The pouch with an incorporated and active loss of integrity indicator according to claim 1, wherein the at least one colorimetric detector is provided in a non-fixed way in one of the first space and the second space in which the at least one colorimetric detector is located.

11. The pouch with an incorporated and active loss of integrity indicator according to claim 1, wherein the at least one colorimetric detector is provided in a fixed way in one of the first space and the second space in which the at least one colorimetric detector is located.

12. The pouch with an incorporated and active loss of integrity indicator according to claim 11, wherein the at least one colorimetric detector is fixed or incorporated in an inner surface of the inner casing, in a lower surface of the outer casing, or in the spacer means.

13. The pouch with an incorporated and active loss of integrity indicator according to claim 1, wherein the at least one tracer gas is selected from a group including oxygen, carbon dioxide, and helium.

14. The pouch with an incorporated and active loss of integrity indicator according to claim 1, wherein the at least one colorimetric detector is an autonomous element, lacking an internal energy source and outside connections.

15. The pouch with an incorporated and active loss of integrity indicator according to claim 1, wherein the at least one colorimetric detector has a large surface, so as to ensure simultaneously that the at least one colorimetric detector is responsive to the tracer gas concentration in the environment in which the at least one colorimetric detector is located and that an observer can note visually when the at least one colorimetric detector has the first color or the second color.

16. The pouch with an incorporated and active loss of integrity indicator according to claim 1, wherein the at least one colorimetric detector is located at a localized site in the pouch, and/or the pouch comprises several colorimetric detectors at several sites in the pouch, the colorimetric detectors being distributed in the pouch.

17. The pouch with an incorporated and active loss of integrity indicator according to claim 16, further comprising several analogous colorimetric detectors in the first space or the second space outside of the first space pouch.

18. The pouch with an incorporated and active loss of integrity indicator according to claim 16, wherein the at least one colorimetric detector includes at least one first colorimetric detector that is responsive to a concentration of a first tracer gas of the at least one tracer gas, the first tracer gas being disposed in the second space outside of the first space pouch, and at least one second colorimetric detector that is responsive to a concentration of a second tracer gas of the at least one tracer gas, the second tracer gas being different from the first tracer gas, the second tracer gas being disposed in the first space, wherein the first tracer gas disposed in the second space outside of the first space pouch has a higher partial pressure than in the first space, and second tracer gas in the first space has a higher partial pressure than in the second space outside of the first space pouch.

19. The pouch with an incorporated and active loss of integrity indicator according to claim 1, wherein one of the first space and the second space outside of the first space pouch includes the at least one tracer gas, and the other of the first space and the second space does not comprise or substantially does not comprise the at least one tracer gas.

20. The pouch with an incorporated and active loss of integrity indicator according to claim 1, wherein the at least one colorimetric detector is generally flat, planar or curved, the curved detector being a pellet or a pseudo-pellet, or a line or a strip, while being rigid, flexible, or semi-flexible semi-rigid.

21. The pouch with an incorporated and active loss of integrity indicator according to claim 1, wherein the pouch is flattened or essentially flattened on itself and suitable for storage, shipping, and handling.

22. The pouch with an incorporated and active loss of integrity indicator according to claim 1, wherein the second, outer casing is configured to allow an outside observer to identify, from the exterior of the outer casing, the color of the at least one colorimetric detector.

23. The pouch with an incorporated and active loss of integrity indicator according to claim 22, wherein the second outer casing is transparent or translucent or comprises a transparent or translucent window for observing the color of the at least one colorimetric detector that is located opposite or in the vicinity thereof.

24. The pouch with an incorporated and active loss of integrity indicator according to claim 1, further comprising an outer protective packaging in which the outer casing, in which the first space pouch is located, is housed.

25. The pouch with an incorporated and active loss of integrity indicator according to claim 1, wherein the pouch indicates a full guarantee of integrity when the at least one colorimetric detector is of the first color, and the first space pouch is evacuated from the second casing and suitable for use.

* * * * *